United States Patent [19]
Rossi

[11] Patent Number: 5,622,820
[45] Date of Patent: Apr. 22, 1997

[54] METHOD FOR AMPLIFICATION AND DETECTION OF RNA AND DNA SEQUENCES

[75] Inventor: John J. Rossi, Glendora, Calif.

[73] Assignee: City of Hope, Duarte, Calif.

[21] Appl. No.: 334,398

[22] Filed: Nov. 3, 1994

Related U.S. Application Data

[63] Continuation of Ser. No. 180,740, Apr. 12, 1988, which is a continuation-in-part of Ser. No. 165,915, Mar. 10, 1988, abandoned.

[51] Int. Cl.$^6$ .............................. C12Q 1/70; C12Q 1/68; C12P 19/34

[52] U.S. Cl. ..................... 435/5; 435/6; 935/77; 935/78

[58] Field of Search ...................... 435/5, 6, 912

[56] References Cited

U.S. PATENT DOCUMENTS

| | | | |
|---|---|---|---|
| 4,503,151 | 3/1985 | Paddock | 536/28 |
| 4,683,195 | 7/1987 | Mullis et al. | 935/17 |
| 4,719,177 | 1/1988 | Baltimore et al. | 935/21 |
| 4,831,124 | 5/1989 | Paddock | 536/28 |
| 4,965,188 | 10/1990 | Mullis et al. | 435/6 |
| 4,994,368 | 2/1991 | Goodman et al. | 435/91.1 |

FOREIGN PATENT DOCUMENTS

| | | | |
|---|---|---|---|
| 0173529 | 3/1986 | European Pat. Off. | 435/5 |
| WO8907149 | 8/1989 | European Pat. Off. | |
| 8203632 | 10/1982 | WIPO | 935/3 |
| 8604146 | 7/1986 | WIPO | 435/6 |

OTHER PUBLICATIONS

Richman et al., J. Infect. Dis. 156(5):823–827 (1987).
Harper, et al. Proc. Natl. Acad. Sci. USA 83: 772–776 (1986).
Chelly et al., Nature 333:858–860 (1988).
Kraus et al., EMBO J.6(3):605–610 (1987).
Slamon et al., Science 224:256–262 (1984).
Storb et al., J. Immunol. 117(1):259–268 (Jul. 1976).
Ratner et al., Nature 313:277–284 (24 Jan. 1985).
Watson et al., Molecular Biology of the Gene, Benjamin/Cummings Publishing Co., 1,163 pages, 1987. p. 650.
Davis et al., *Basic Methods in Molecular Biology*, Elsevier, New York, 1986, pp. 143–146.

*Primary Examiner*—Stephanie W. Zitomer
*Attorney, Agent, or Firm*—Rothwell, Figg, Ernst & Kurz

[57] ABSTRACT

A method for detecting false negative and false positive results in a method of detecting and identifying specific human nucleic acid sequences contained in human nucleic acids in a human blood or tissue sample, comprising: (1) amplifying at least one portion of the specific nucleic acid sequence present in the sample and simultaneously simplifying a marker sequence; (2) transcribing the amplification products with an RNA polymerase to produce multiple RNA copies of each copy of specific nucleic acid sequence comprising the amplification product; and (3) identifying the transcription products.

16 Claims, 13 Drawing Sheets

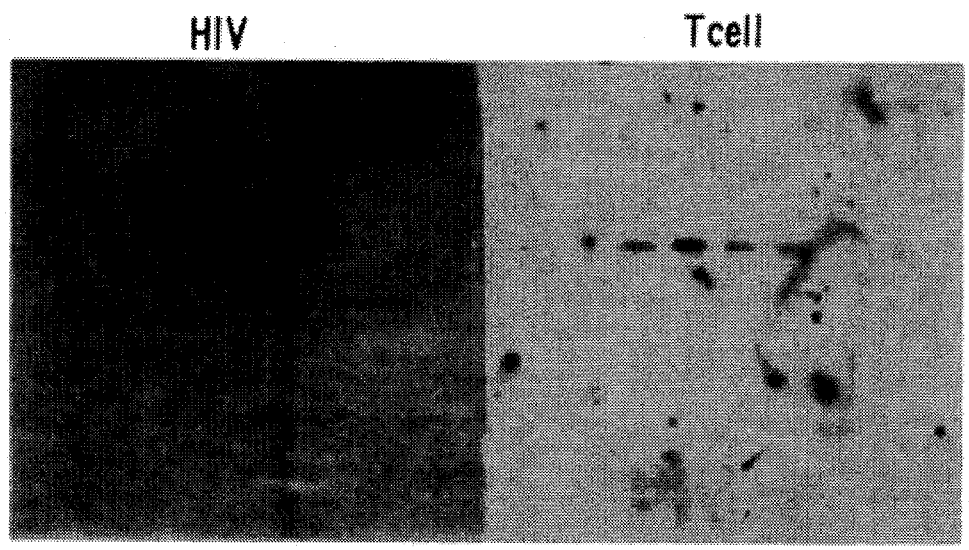
FIG. 9A
 
FIG. 9B     FIG. 9C

METHOD FOR AMPLIFICATION AND DETECTION OF RNA AND DNA SEQUENCES

This application is a continuation of application Ser. No. 07/180,740, filed Apr. 12, 1988, which is a continuation-in-part of application Ser. No. 07/165,915, filed Mar. 10, 1988 now abandoned.

This invention relates to methods for amplifying, detecting, and identifying specific sequences from RNA or DNA templates.

Amplification of an RNA template is particularly advantageous for detecting retroviruses, such as human immunodeficiency virus (HIV or human T-lymphotropic virus HTLV III/LAV). HIV has been shown to be the etiological agent of acquired immune deficiency syndrome (AIDS). Direct detection of HIV-1 nucleic acid sequences in patient tissue or blood samples is possible in only a small fraction of cases due to the low percentage of infected cells. Shaw, B. M., et al., *Science* 226: 1165–1171 (1984). At present, rapid clinical detection of HIV-1 infection in humans is difficult since tests depend on the presence of circulating serum antibodies against HIV-specific antigens. Such tests are not 100% reliable as reported Groopman, J. E., et al., *Blood* 66: 742–744 (1985), and Fischinger, P. J., et al., *AIDS Etiology Diagnosis, Treatment and Prevention*(Ed. DeVita, V. T., et al.) 55–58 (J. B. Lippincott Co., Philadelphia, Pa.) (1985). A further problem with the detection of serum antibodies is that such antibodies may appear weeks or months after infection by HIV-1, and thereby diminishing the utility of serologic tests for early detection of infection.

Direct detection of HIV-1 nucleic acid sequences in peripheral blood samples from AIDS or AIDS-related complex (ARC) patients via Southern blot analysis, Shaw, B. M., et al., *Science* 226: 1165–1171 (1984) or in situ hybridization, Harper, M. E, et al., *Proc. Nat. Acad. Sci. USA* 83: 772–776 is inefficient.

It has recently been shown by Saiki, R. K., et al., *Science* 230: 1350–1354 (1985) that small amounts of DNA samples, undetectable with standard nucleic acid hybridization methods, can be specifically detected after amplification. This method makes use of repeated synthesis of target nucleic acid sequences flanked by oppositely oriented converging primers, and is referred to as the polymerase chain reaction, or PCR. The PCR was initially used to amplify the β-globin genomic sequence for the prenatal diagnosis of sickle cell anemia. Id.; Mullis, K., et al., *Methods in Enzymology* 155: 335–350 (1987).

In general, the modified method uses reverse transcriptase in the initial amplification cycles to produce DNA transcripts from RNA templates. An advantage of amplifying an RNA template rather than a DNA template is greater resolution because expression of the messenger RNA (mRNA) in higher eukaryotic cells is selective and often tissue specific or time dependent. Therefore amplification of RNA can rely on a less complex template.

This invention provides a test to rapidly detect and identify HIV-1 sequences or any other RNA or DNA sequences for which some sequence information is known. This invention further provides means for preventing false positive and false negative AIDS diagnoses via a co-amplification system for simultaneous amplification of other important cellular marker sequences. Means are also provided for allowing for quantitation of the initial amounts of template used. The method described in application Ser. No. 06/941,379 and Ser. No. 07/143,045 aforesaid modified PCR technique has been further modified according to the present invention by incorporating one or more transcription steps as well as an internal standard into the technique. The transcription steps enhance the amplification of target nucleic acid sequences, thereby facilitating detection of amplified products.

SUMMARY OF THE INVENTION

In general, the invention features methods of detecting and identifying specific human nucleic acid sequences contained in human nucleic acids in a human blood or tissue sample, comprising amplifying at least one portion of the specific nucleic acid sequence present in the sample, transcribing the amplification product with an RNA polymerase to produce multiple RNA copies of each copy of specific nucleic acid sequence comprising the amplification product, and identifying the transcription product.

In preferred embodiments the recognition sequence for bacteriophage T7 RNA polymerase is appended to the 5' end of at least one of the amplification primers. After transcription of amplification product and prior to identification of product, further transcription and amplification steps can be carried out.

In other preferred embodiments, the invention features methods of detecting and identifying HIV-1 sequences, including a co-amplification system for simultaneous amplification of other important cellular marker sequences, such as sequences for beta-actin, T-cell receptor, and T4 (CD4) receptor.

Other advantages and features of the invention will be apparent from the following description of the preferred embodiments thereof, and from the claims.

DESCRIPTION OF THE DRAWINGS

FIGS. 9A and 9B show photographs of autoradiograms of amplified HIV-1 3'ORF and T-cell receptor beta-chain constant region template probed with HTLV-C (left panels) and T-cell receptor (right panels) hybridization probes. In Panel A, RNA template was obtained from HIV-1 infected H9 cells; in panel B DNA template was obtained from the pGM92+21 transcript (a), HIV-1 infected H9 cells (b), and a diagnosed AIDS patient (c).

DESCRIPTION OF THE PREFERRED EMBODIMENT

The present invention provides methods for increasing the level of amplification of RNA or DNA template by incorporating at least one transcription reaction in the RT PCR amplification technique. This transcription step is carried out by allowing an RNA polymerase to faithfully make multiple copies of DNA template generated by the RT PCR amplification technique. Inclusion of one or more transcription steps within the framework of the aforesaid modified PCR technique reduces the labor involved in the amplification technique, while substantially increasing the level of amplified end product.

In preferred embodiments a portion of the recognition sequence of the bacteriophage T7 RNA polymerase is appended to at least one of the oligodeoxyribonucleotide primers.

In other embodiments, internal standards, a co-amplification system for enabling accurate diagnosis of HIV-1 infection, and non-radioisotopic detection methods for amplified oligonucleotide product are provided.

The distal portion of the HIV virus within the 3' open reading frame (ORF) was chosen for amplification because of the limited sequence polymorphism in this region among different viral isolates. However, the methods of the present invention are not limited to amplifying HIV-1 and can be used to amplify any RNA or RNA sequence for which some sequence information is known.

Figure 1:
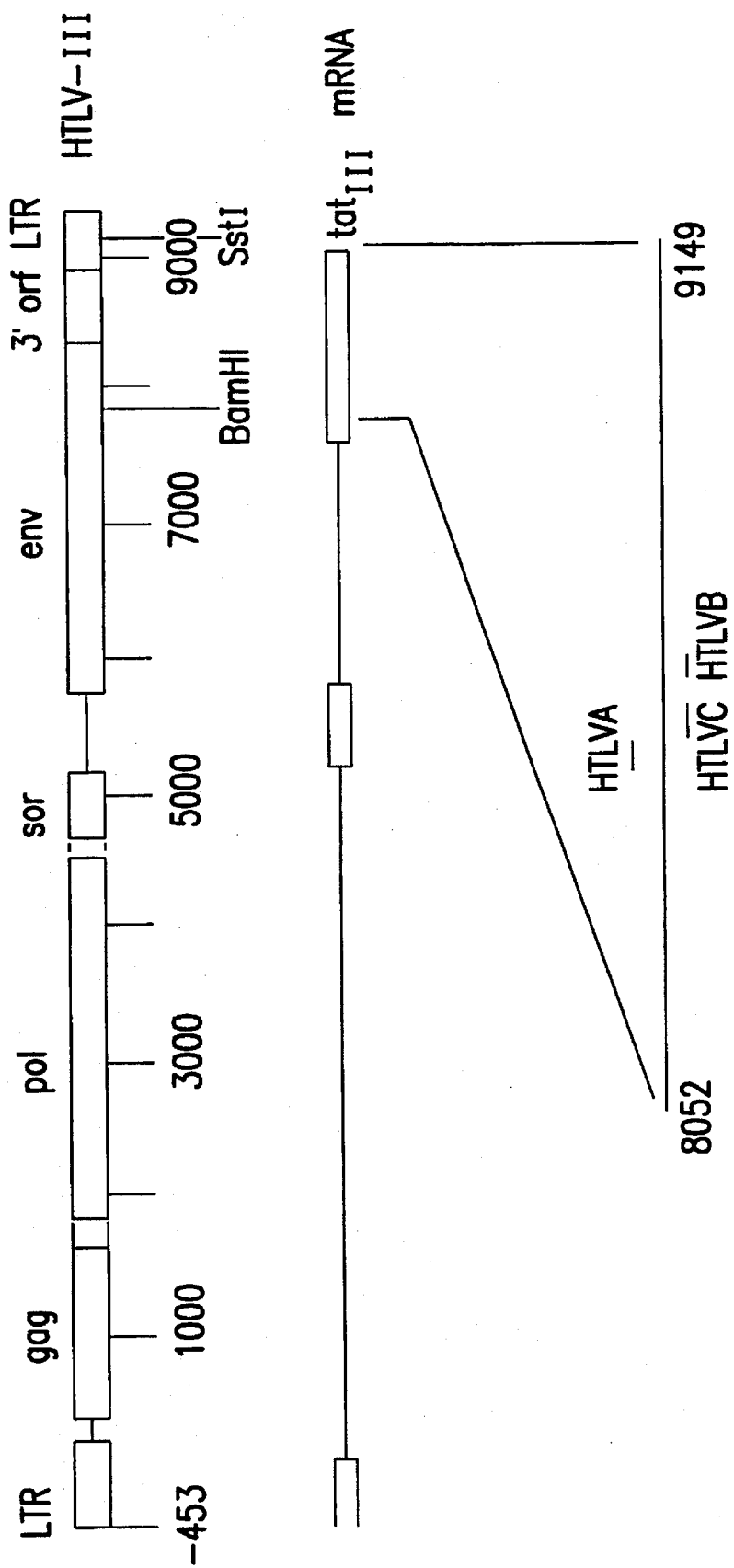
FIG. 1 shows a diagram of the entire HIV-1 virus and the region of the virus amplified by the method of the present invention. Genes and long terminal repeats (LTR's) are shown as open boxes within the 3' ORF amplification region. Positions of oligodeoxyribonucleotide amplification primers HTLV-A and HTLV-B and internal oligodeoxyribonucleotide probe HTLV-C are shown.

FIG. 1 shows the region of amplification and the preferred synthesized oligodeoxyribonucleotide amplification primers (HTLV-A and B) and internal probe (HTLV-C). The genes and long terminal repeats (LTRs) are represented by open boxes. The 1.1 kb BamHI-Sst-I fragment is enlarged and shown below the entire virus. This fragment contains the amplification region which lies within the 3' ORF region.

In the following examples HTLV-A and HTLV-B were added to RNA or DNA template. Primer HTLV-A is preferably a sense oligodeoxyribonucleotide with the sequence 5'ATGCTGATTGTGCCTGGCTA 3' encoding nucleotides 8950–8969. Primer HTLV-B is preferably an antisense oligodeoxyribonucleotide with the sequence 5'TGAATTAGC- CCTTCCAGTCC 3' encoding nucleotides 9100 to 9081. HTLV-B, being complementary to the viral RNA or DNA template, anneals to the template and serves as the primer for the synthesis of the first strand of DNA by AMV reverse transcriptase. Once the first strand of DNA is synthesized using primer HTLV-B and the original template, primer HTLV-A primes the synthesis of the second strand of DNA which is mediated by a DNA polymerase. Upon completion of this reaction, samples are cycled through repeated denaturation, annealing and polymerization cycles. Treatment with ribonuclease A in later cycles facilitates primer annealing by degrading RNA which may compete for the binding of oligonucleotides.

Amplified samples are assayed or detected by various known methods. For example, alkaline Southern blot analysis as described by Reed, K. C., et al., *Nucl. Acids Res.* 13: 7207–7221 (1985) and Southern, E. M., *J. Mol. Biol.* 98: 503–517 (1975) using as a probe a third synthetic oligodeoxyribonucleotide (HTLV-C) complementary to a region within the amplified segment can be used. A preferred internal probe used for detection of the amplified segment is an antisense oligodeoxyribonucleotide, HTLV-C, with the sequence 5'AAGTGGCTAAGATCTACAGCTGCCT 3' encoding nucleotides 8642 to 8618. Oligodeoxyribonucleotide internal probes used in accordance with the present invention are labelled preferably at their 5' ends using adenosine 5'-[$\gamma^{32}$P] triphosphate ($\gamma^{32}$P-ATP) and T4 polynucleotide kinase as described by Murakami, A., et al., *Biochem.* 24: 4041–4046 (1985). Other detection methods are illustrated in the examples.

Examples of DNA polymerase that can be used to perform the RT PCR technique are DNA polymerase I (Klenow fragment) at 37° C. and DNA polymerase isolated from *Thermus aquaticus* (*Taq*) as reported by Chien, A., et al., *J. Bacteriol.* 127: 1550–1557 (1986) at 74° C. The *Taq* enzyme is heat stable and, unlike Klenow, is not inactivated during the denaturing steps. In cases where the Taq enzyme is used, but lower polymerization temperatures are used, the polymerization reaction is carried out for approximately 5 minutes. In general following transcription with reverse transcriptase, approximately 2.5 units of *Taq* I polymerase are added to the reaction mixture, and pH, divalent cations and dNTPs are accordingly adjusted. Polymerizations are typically carried out at 65°C. to 74° C., depending on the amplification primers used.

According to the present invention the amplification of RNA or DNA sequences using the RT PCR technique is increased by about 50 to about 100 fold by incorporating at least one transcription step into the technique.

A portion of recognition sequence for the bacteriophage T7 RNA polymerase, as described by Studier, F., et al., *J. Mol. Biol.* 189: 113–130 (1986) and Dunn, J., et al., *J. Mol. Biol.* 166: 477–535 (1983) is first appended to the 5' end of at least one of the oligodeoxyribonucleotide amplification primers to be used in performing the aforesaid modified PCR technique. For example, for amplifying HIV-1 sequences from the 3' ORF region, primer HTLV-A was so modified and was denoted HTLV-AT7 as seen below:

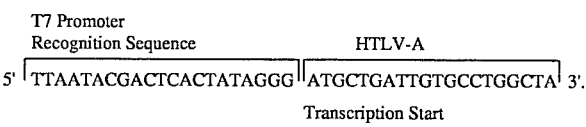

HTLV-AT7 contains the 20 bases of primer HTLV-A complementary to the 3' ORF region of HIV-1 described previously, and 21 bases at the 5' end of the primer which comprise recognition sequences for the bacteriophage T7 RNA polymerase and which are not complementary to HIV-1. The presence of these non-complementary bases at the 5' end of the primer does not interfere with the primer's priming ability.

In performing the aforesaid modified PCR technique with HTLV-AT7 and HTLV-B instead of with HTLV-A and HTLV-B, HTLV-B primes the first strand synthesis mediated by reverse transcriptase. Then HTLV-AT7 primes the second strand synthesis mediated by a DNA polymerase, to form a single stranded T7 sequence. In following rounds the T7 sequence is fully base-paired to the complementary strand derived from HTLV-B mediated priming. After several rounds of polymerization, there is a sizeable population of molecules containing the double stranded T7 promoter sequence attached to the amplified sequences. The transcriptional amplification is then carried out by adding several units of T7 RNA polymerase and nucleoside triphosphates to the amplification mixture. The T7 RNA polymerase produces from about 50 to about 100 RNA copies of the 5' strand of the double-stranded targeted DNA sequence in about a 10–30 minute incubation period.

Figure 2:
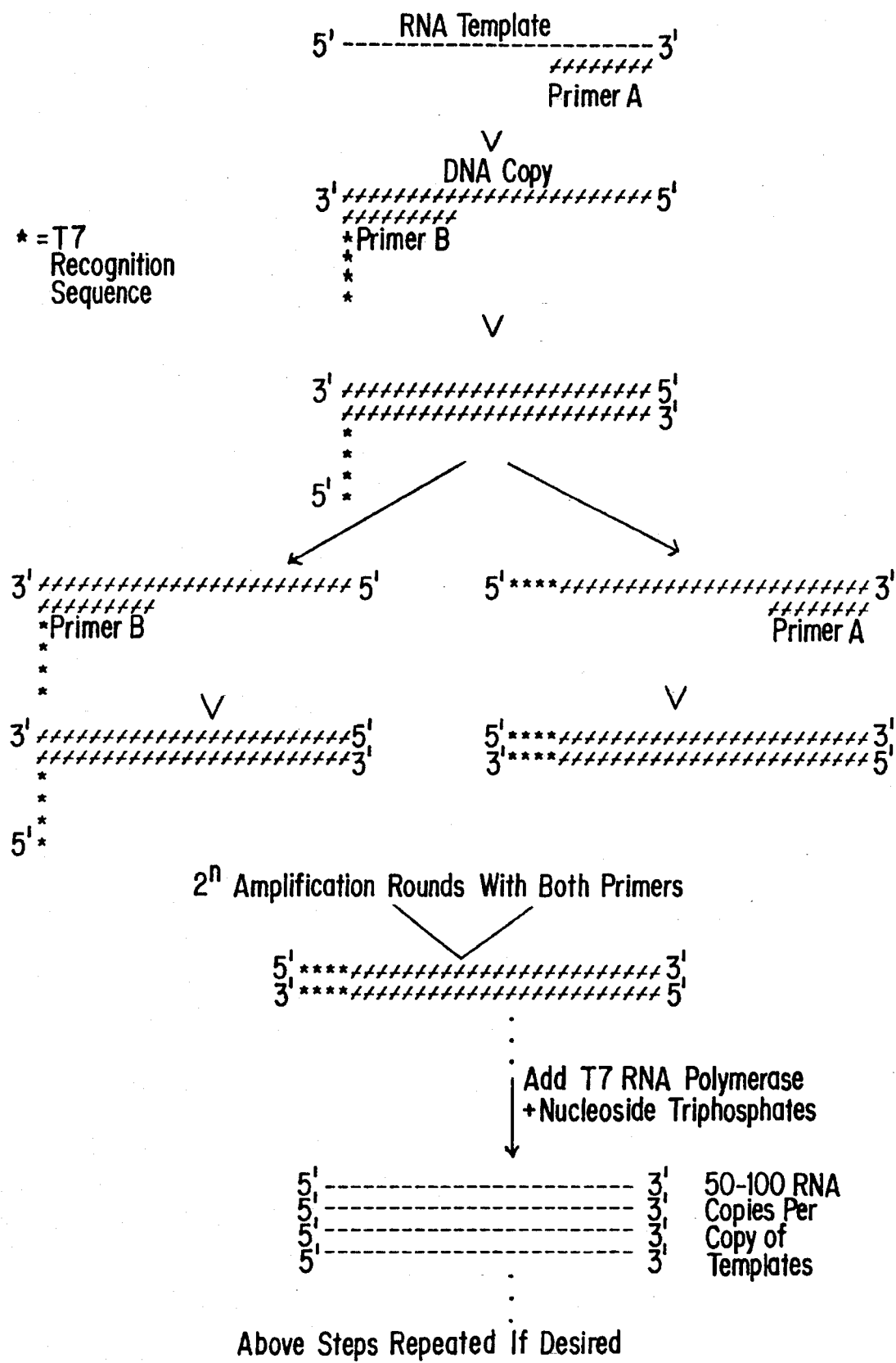
FIG. 2 is a general schematic diagram depicting the steps of the method of the invention.

FIG. 2 shows schematically the course of the amplification and transcription reaction.

Figure 3:
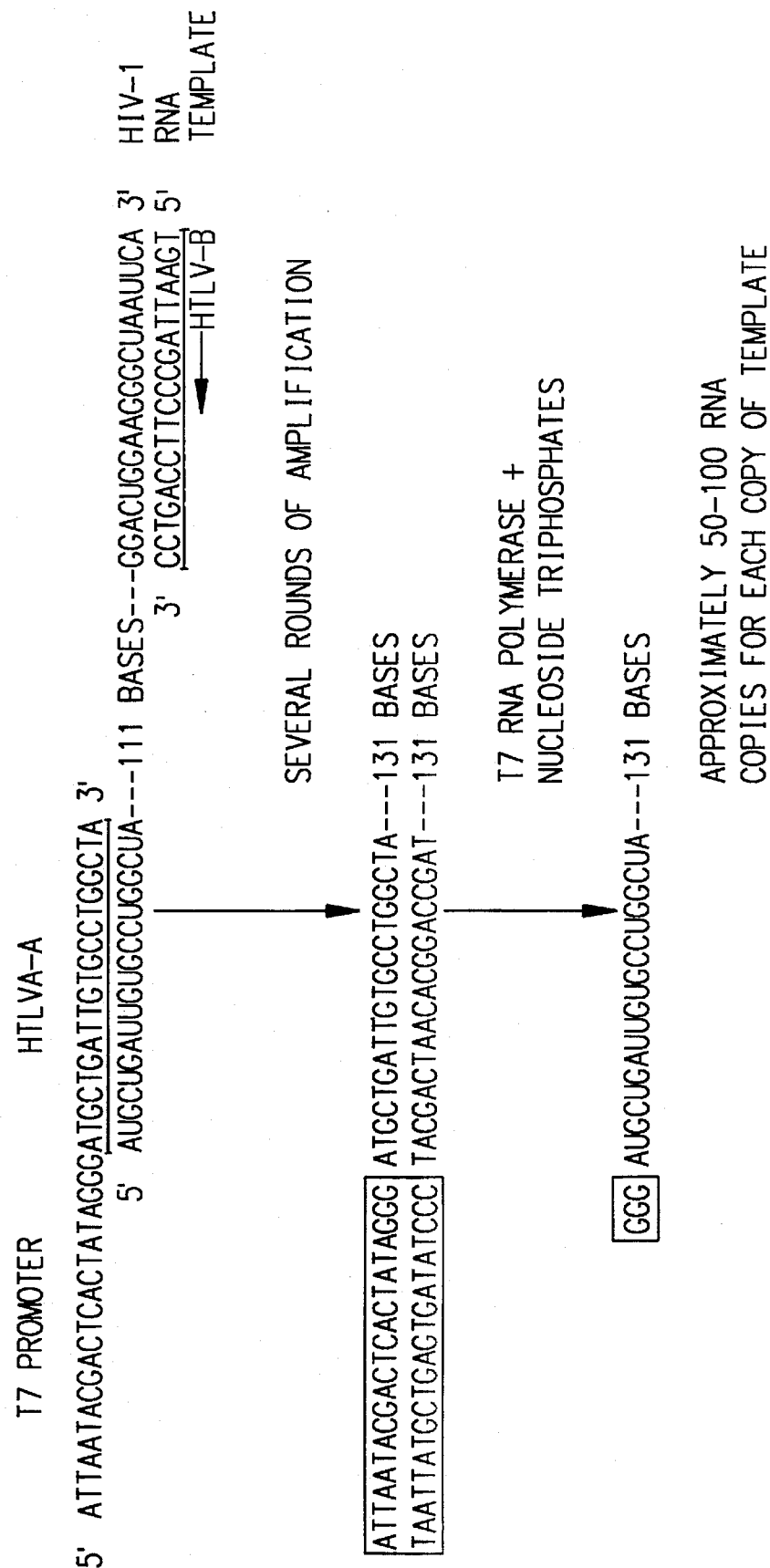
FIG. 3 is a schematic diagram showing the method of the invention using an HIV-1 template.

FIG. 3 shows schematically the course of the amplification and transcription reactions for an HIV-1 template using primers HTLV-AT7 and HTLV-B.

The following example illustrates use of the RT PCR technique and the transcriptional amplification enhancement of the present invention.

EXAMPLE 1

Two plasmids harboring the 3' ORF region of HIV-1 were used. A 1.1 kilobase-pair BamHI-SstI fragment isolated from pBH10 (Biotech Research Laboratories) was subcloned in both orientations into the transcriptional vector pGEM2 (Promega Biotec), generating the plasmids pGM92 and pGM93. Plasmid pGM92, when linearized with EcoRI, was the source of the plus (sense)-strand in vitro transcripts containing the 3' ORF region. A derivative of pGM92 was constructed by inserting a synthetic sequence into the unique KpnI site. The insert used had the sequence 5' CACA-CAAGGCTACTTCGGTAC 3'. The resulting plasmid (pGM92+21) produced a transcript which is 21 nucleotides longer than that derived from pGM92.

Amplification was performed in 1X amplification buffer (10 mM tris-HCl, pH 7.5; 10 mM $MgCl_2$; 66 mM NaCl; and 1 mM dithiothreitol), a large molar excess (1.5 mM) of each of the four deoxynucleoside triphosphates (dNTP), and 1.0 μm of each of the oligodeoxynucleotide primers HTLV-A or HTLV-AT7 and HTLV-B, and varying amounts of RNA template as described further in the following examples in a final reaction volume of 100 μl.

For the first amplification cycle, RNA template was heated to 95° C. for two minutes, centrifuged for 5 seconds, and then cooled to 37° C. for two minutes to anneal template to primer. Then 1.0 μl of AMV reverse transcriptase (2.0 units, Life Sciences or BioRad) diluted in amplification buffer was added to the reaction mixture for a two minute incubation at 37° C. in order to extend the complementary primer (HTLV-B) annealed to the viral RNA template. Amplification cycles 2–6 were carried out as above by reheating the reaction mixture to 95° C. for two minutes and repeating the cycle sequence, except that both reverse transcriptase and 0.5 units DNA polymerase I (Klenow) (Boehringer Mannheim or BioRad) were added for elongation of the primers. In cycle 7, RNase A was added (0.45 μg) to reduce the complexity of the RNA and to facilitate primer hybridization, and only DNA polymerase I was used. For subsequent amplification cycles only the DNA polymerase was added at 1 unit per 10 cycles. After completion of the last amplification cycle, samples were placed on ice.

For amplification of DNA template, reverse transcriptase and RNase A are not used in the amplification procedure, but otherwise the procedure is as described above for RNA template.

Following the desired number of rounds of amplification the transcription reaction was carried out by extracting the amplification mixture two times with phenol, one time with dichloromethane, and precipitated with 3 volumes of ethanol for 5 minutes at room temperature. The resulting pellet was washed once with 70% ethanol, dried, and resuspended in 50 μl of 10 mM Tris, pH 7.5 and 1 mM EDTA. Either an aliquot of amplified template mixture or the whole mixture can be transcribed.

Approximately $5 \times 10^{-3}$ to $10^{-2}$ pmoles of template were added to a 20 μl reaction mixture consisting of 500 μm each of ATP, CTP, GTP, and UTP [or 50 μM UTP and 10–20 microcuries of $^{32}$P-UTP (Dupont-New England Nuclear 2000 Ci/mmol)] in 40 mM Tris-HCl, pH 8.0, 20 mM $MgCl_2$, 10 mM NaCl, 1 mM dithiothreitol, and 20 units of placental ribonuclease inhibitor. T7 RNA polymerase (BioRad) was added to a final concentration of 10 units and the reactions were carried out at 37° C. for 30–60 minutes. The reactions were terminated by phenol extraction followed by ethanol precipitation.

If additional amplification rounds are to be carried out, primers HTLV-A and HTLV-B are added, and if additional amplification rounds are to be carried out and then the products transcribed further by T7 RNA polymerase, primers HTLV-AT7 and HTLV-B are added. The amplifications and transcriptions are then performed as described above.

Radiolabeled transcription products were analyzed by direct autoradiography by resuspending the samples in 6 μl of 90% formamide containing 0.05% each of xylene, cylanol, and bromphenol-blue, heating at 95° C. for 1 minute, and electrophoresing in a 6% polyacrylamide, 7M urea gel using 0.5 X TBE buffer. The gels were then autoradiographed using Kodak XAR-5 film at –70° C. with a Dupont Cronex intensifying screen.

Transcription products not radiolabeled were detected by converting the RNA to DNA via a few more amplification rounds and then electrophoresing them in a 1.8% agarose gel containing 0.5 μg/ml ethidium bromide and 0.5 X TBE buffer for 1 to 2 hours at 1.5 v/cm. After the DNA was visualized, the gel was soaked for 10 minutes in 0.4M NaOH as described by Reed, K. C., et al., Nucl. Acids Res. 13: 7207–7221 (1985), and vacuum blotted onto a nylon membrane (Zeta-Probe (BioRad)) for 30–60 minutes using 0.4M NaOH.

After transfer, the nylon membranes were briefly neutralized in 2XSSC (0.3M NaCl, 0.03M NaCitrate, pH 7.0). The amplification material was then hybridized with 1 pmole/ml of $^{32}$P-labelled internal probe HTLV-C in 6X SSPE (1.0M NaCl, 0.06M $NaPO_4$, pH 7.0, 0.006M EDTA); 7% SDS; and 0.5% rehydrated, powdered skim milk [(Alba) "blotto"] or 6X SSPE, 1.0% SDS, 0.5% blotto, and 10 μg/ml sonicated, denatured herring sperm DNA for 3–12 hours at 65° C. In all cases, the hybridized filters were washed three times with 6X SSC (0.95M NaCl, 0.095M Na Citrate) at 65° C. for 5 minutes each. The filters were then autoradiographed as described above.

Figure 4:
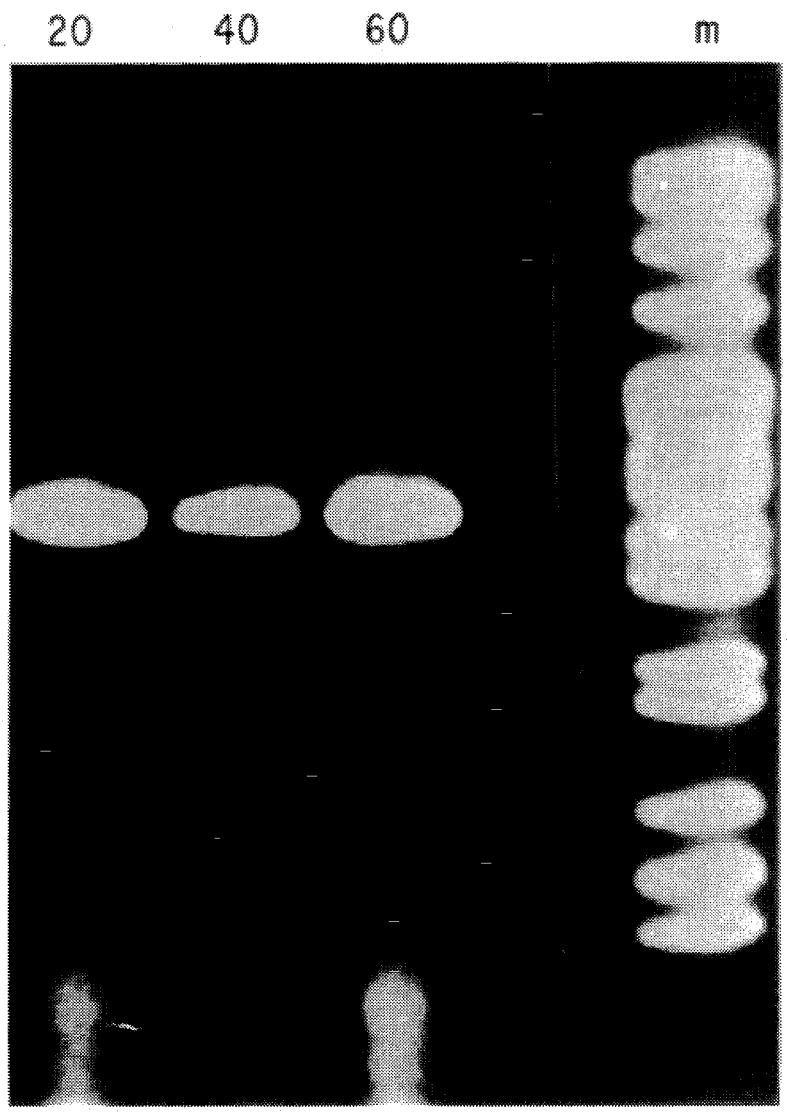
FIG. 4 shows a photographic negative of an autoradiogram showing the time course of transcription of amplified HIV-1 template.

FIG. 4 shows a photographic negative of an autoradiogram showing the time course of transcription of amplified HIV-1 sequences. Amplification primers HTLV-AT7 and HTLV-B were used. One tenth of the amplification reaction mixture was used for the transcription reaction. Aliquots of the transcription reaction mixture were withdrawn at 20, 40, and 60 minutes after the addition of T7 RNA polymerase and subjected to autoradiography. The transcription products were labelled with $^{32}$P-tagged UTP. The FIG. 4 autoradiogram shows the transcription reaction went to saturation in 20 minutes.

EXAMPLE 2

3' ORF RNA template from pGM92 and a derivative of pGM92 constructed by inserting a 21 base insert (5'CACA-CAAGGCTACTTCGGTAC) within the unique KpnI site (pGM92+21) were amplified for 10 rounds by the RT PCR technique described in Example 1 using primers HTLV-AT7 and HTLV-B. One half of the reaction mixture was further amplified by transcribing the DNA with T7 RNA polymerase for 30 minutes. The other half of the reaction mixture was held on ice. Both samples were then amplified another 5 rounds by the RT PCR technique using the same primers. The sample that had been transcribed with T7 polymerase was amplified using reverse transcriptase followed by DNA polymerase I; the sample that was amplified but not transcribed used only DNA polymerase I. The previously transcribed sample was once again transcribed by a reaction that included $^{32}$P-UTP.

Figure 5:
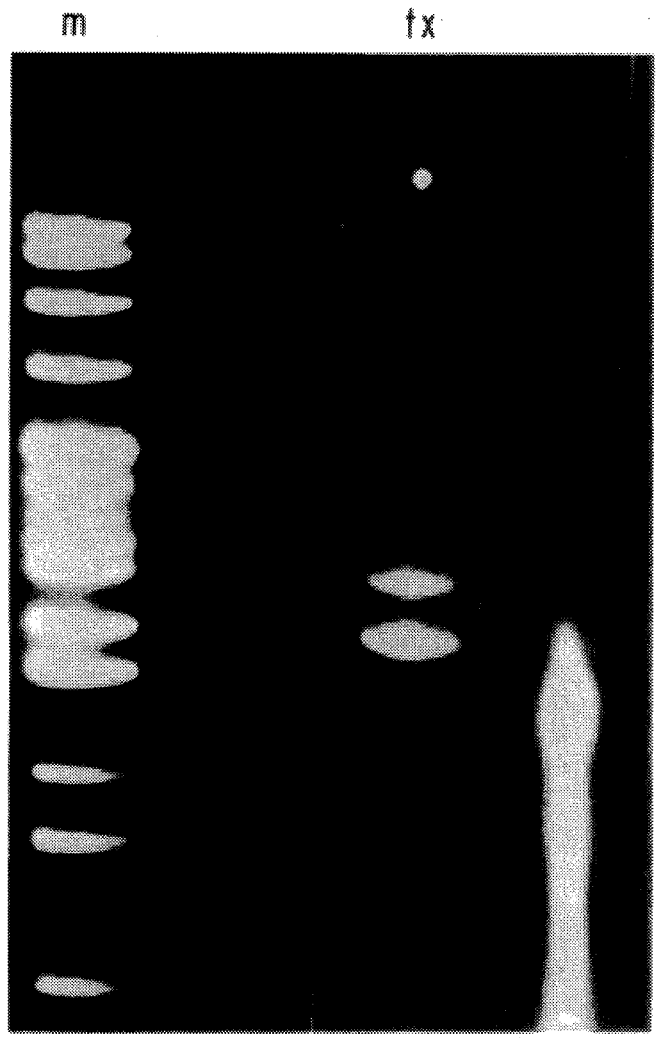
FIG. 5 shows a photographic negative of an autoradiogram of amplified HIV-1 template and HIV-1 template incorporating an internal standard of 21 extra bases in the right lane and in lane "tx" HIV-1 template and the internal standard template which were amplified and then transcribed with T7 RNA polymerase.

FIG. 5 shows an autoradiogram of the above-described transcriptional enhancement of the RT PCR technique. There was a clear difference in the amount of product detected from the reaction containing transcription steps and the reaction that did not include transcription. The lane labelled "tx" contains product that was transcribed by T7 RNA polymerase as well as amplified. The unlabeled lane contains amplified product that was not transcribed. In the tx lane the upper and lower bends contain respectively the amplification products of the pGM92+21 template and the pGM92 template. In the lane containing non-transcribed product, an upper expected band is barely visible, while a lower band is only faintly visible. The spot of bright material at the bottom of the lane is unincorporated $^{32}$P-UTP which was retarded in its gel mobility by an air bubble in the acrylamide.

EXAMPLE 3

0.1 ng of RNA template prepared from pGM92 and pGM92+21 was amplified using primers HTLV-AT7 and HTLV-B. pGM92+21 serves as an internal control. After 12 amplification rounds, 1/20 of the amplified sample was phenol extracted, ethanol precipitated and resuspended in a 20 µl transcription reaction as described in Example 1. P$^{32}$-UTP (10 µcuries) was included in the transcription reactions, which were allowed to proceed for 30 minutes. The resulting reaction mixtures were electrophoresed in an 8% polyacrylamide-8M urea gel in TBE buffer. The gel was then autoradiographed for 2 hours at –70° C. with an intensifying screen.

Figure 6:
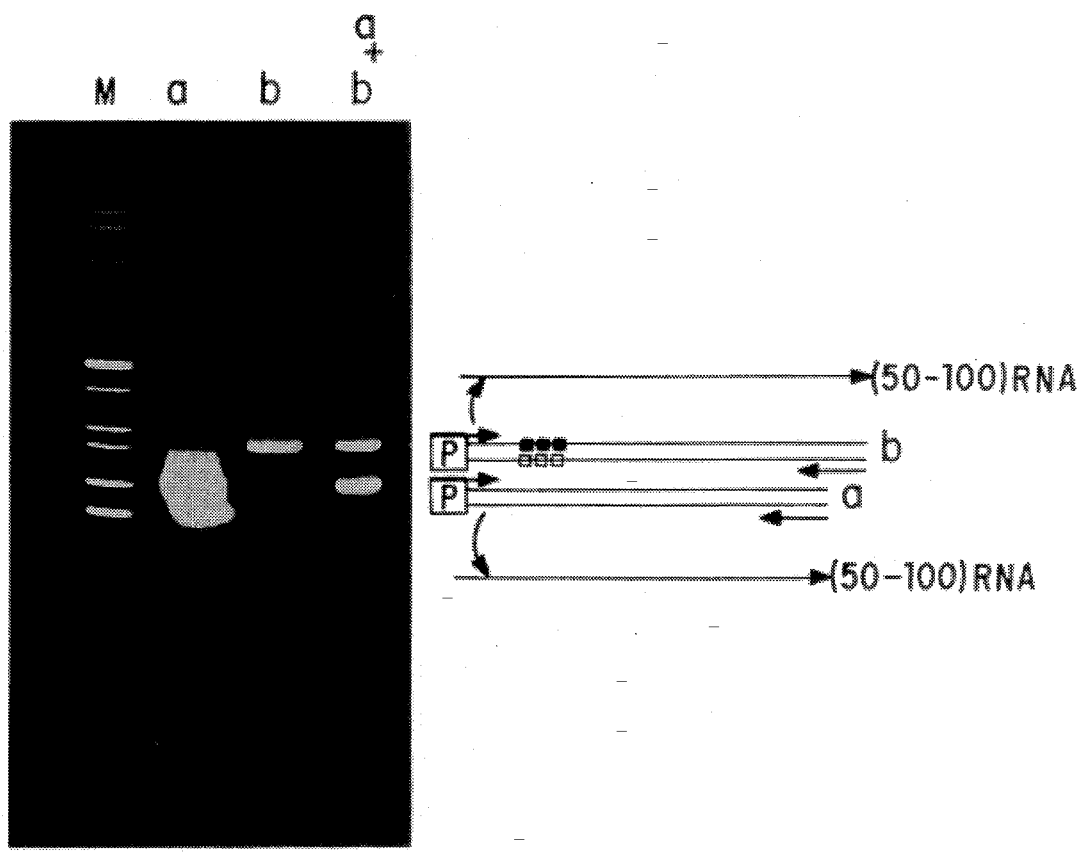
FIG. 6 shows a photographic negative of an autoradiogram of amplified and T7 RNA polymerase transcribed HIV-1 template (a), HIV-1 template which included an extra 21 base sequence (b), and approximately equimolar mixtures of both templates (a+b).

A photograph of the resulting autoradiogram is shown in FIG. 6. In FIG. 6 lane "M" is HpaII digested pBR322; "a" is amplified-transcribed pGM 92 template; "b" is amplified-transcribed pGM92+21 template; and "a+b" is an approximately equimolar mixture of amplified-transcribed pGM 92 and pGM92+21 templates.

The diagram to the right of the autoradiogram photograph illustrates schematically the procedure used. "P" represents the bacteriophage T7 promoter sequence which is incorporated into the amplified DNA. The small squares in the "b" template represent the 21 base sequence inserted between the priming sites of the pGM92+21 template. Lane "a" shows strong amplification of HIV-1 sequences.

Analysis of lane "a+b" shows that when equimolar amounts of RNA from both pGM92 and pGM92+21 were amplified by the methods of the present invention, both templates were simultaneously amplified with approximately equivalent efficiencies, with the upper band representing the internal control pGM92+21 amplification and product and the lower band representing pGM92 product.

EXAMPLE 4

HIV-1 RNA from a patient blood sample was amplified using a primer containing the promoter sequence. HIV-1 RNA was extracted from lymphocytes isolated from peripheral blood. One µg of patient RNA was amplified for 15 rounds with the HTLV-AT7 and HTLV-B primers. Then 1/20 of the reaction mixture was withdrawn, mixed with approximately 50 ng of pGM92+21 RNA as an internal standard, and the two samples were amplified with AMV reverse transcriptase and then DNA polymerase I for 10 additional rounds using the same primers. One twentieth of the resulting mixture was phenol extracted, ethanol precipitated, and then included in a transcription reaction as described above. The amplified products were subjected to autoradiography for approximately 12 hours at –70° C. with an intensifying screen.

Figure 7:
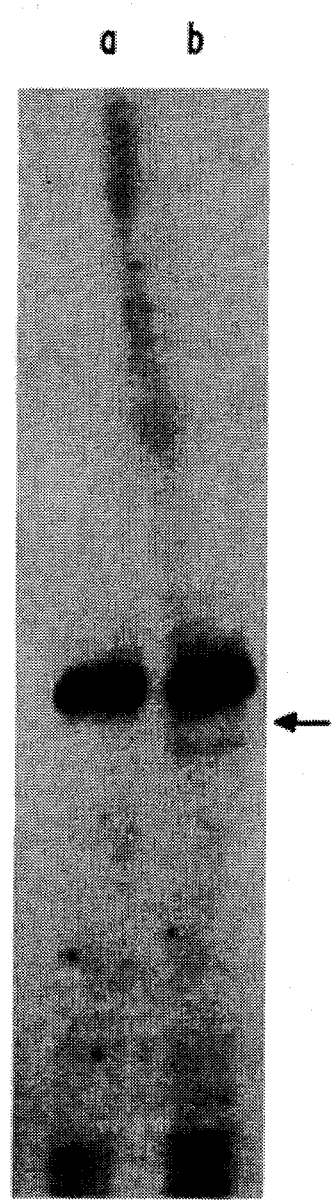
FIG. 7 shows a photograph of an autoradiogram of amplified and transcribed HIV-1 from a patient sample.

A photograph of the resulting autoradiogram is shown in FIG. 7. Specific transcripts of HIV-1 sequences were readily detected after the transcription with T7 RNA polymerase. Lane "a" contains amplified DNA-RNA from pGM92+21 alone; lane "b" contains amplified DNA-RNA from pGM92+21 and the patient sample. The arrow points to the lower band which is the amplified patient sample product whereas the upper band represents the larger pGM92+21 amplified product.

In order to validate results of a given HIV-1 amplification, it is useful to have additional targets for priming and amplification other than the 3'ORF segment described above. An additional target for that purpose is the 5'LTR region of the virus. The sequences to be amplified are between the 5' start point of transcription and the first major 5' splice site (nucleotides +88 through +284 of the published sequence of Ratner, L., et al., *Nature* 313: 277–284 (1985)).

Positive results from amplification of 3'ORF and 5'LTR targets allow for a more accurate diagnosis for HIV-1 infection, minimizing the chance of false positive diagnosis. The problem of false negative readings from, for example, destruction of HIV-1 nucleic acid in processing, can be overcome by including a set of amplification primers for an abundant mRNA in the same reaction set as the HIV-1 primers. The beta-actin mRNA sequence (nucleotides 1883–2250 of the sequence of Ng., S.-Y., et al., *Mol. Cell. Biol.* 5: 2720–2732) (1985)is so used as an internal standard. For example, if neither HIV-1 nor beta-actin amplification is observed, either the amplification reaction failed, or the RNA preparation is inadequate. Other sequences expected to be present in HIV infected cells, the beta chain of the constant region of the T-cell receptor, or the T4(CD4) receptor are also used as internal standards to insure against false negative diagnosis.

For amplification of HIV-1 5'LTR sequences, the first primer is preferably a sense oligodeoxyribonucleotide with the sequence 5' TGAGTGCCTCAAGTAGTGTGT GCCC 3', the second primer is preferably an antisense oligodeoxyribonucleotide with the sequence 5' GTCGCCGC- CCCTCGCCTCTTGCCGT 3', and a preferred internal probe complementary to a region within the amplified segment is an antisense oligodeoxyribonucleotide with the preferred sequence 5' CGAAAGGGAAACCA- GAGCTCTCTCG 3'.

In order to amplify the above-described beta-actin sequence, the first primer is preferably a sense oligodeoxyribonucleotide with the sequence 5' CTCATTGCCAATG- GTGATGACCTG 3', the second primer is preferably an antisense oligodeoxyribonucleotide with the sequence 5' GCTATCCCTGTACGCCTCTGGC 3' and the internal probe is an antisense oligodeoxyribonucleotide with the preferred sequence 5' CGGTGAGGATCTTCATGAGG- TAGTC 3'.

In the following example, HIV 5'LTR and beta-actin sequences are co-amplified.

EXAMPLE 5

One microgram samples of total RNA were mixed with equal amounts of the above-described HIV 5'LTR specific primers and primers for beta-actin mRNA. The sequences were amplified for 30 rounds. The first few amplification rounds were carried out with reverse transcriptase; remaining rounds were carried out with 2.5 units of *Taq* I polymerase as described above using a Gene-Amp Kit (Perkin-Elmer, Cetus). Electrophoresis, blotting, and hybridization conditions were performed as described in Example 1.

Figure 8A:
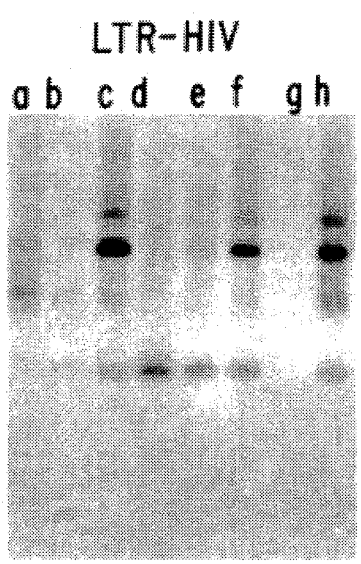
FIG. 8 shows photographs of autoradiograms of amplified HIV-1 and beta actin sequences using various template sources and one or both sets of amplification primers for HIV-1 and beta actin. The left panel was probed with an HIV-1 hybridization probe; the right panel was probed with a beta actin hybridization probe.
Figure 8B:
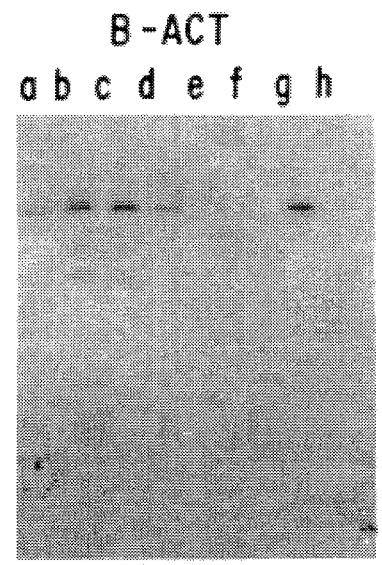

The sources of the samples and primers included in each reaction represented in FIG. 8 are: lanes a and b-human lung tissue from an autopsy with both 5'LTR and beta-actin primers; lane c¯HIV-1 infected H9 cells with both 5'LTR and beta actin primers; lane d¯uninfected H9 cells with both 5'LTR and beta actin primers; lane e¯HCMV DNA with both 5'LTR and beta-actin primers; lane f¯HIV-1 infected H9 cells with only 5'LTR primers; lane g¯uninfected H9 cells with only beta-actin primers; and lane h¯HIV-1 infected H9 cells with only 5'LTR primers. The left panel represents probing with the 5'LTR probe. After autoradiography, the nylon filter was stripped of the 5'LTR probe and reprobed with the beta-actin probe.

As seen in the left panel, the amplification bands for the amplified HIV-1 segment are seen in lanes c, f, and g; while the amplification bands for amplified beta actin sequence are seen in lanes a, b, c, d, and g, but not in lanes e, f, and h. Such amplification bands are expected because HIV-1 infected H9 cells, a T-cell line, are expected to have high levels of both T-cell receptor and HIV-1 products. In contrast, peripheral blood samples from an AIDS patient had low levels of T-cell receptor product, but high levels of HIV-1.

One of the hallmarks of active HIV-1 infection is a reduced number of T4 lymphocytes relative to other classes of T-cells. The present invention provides methods for amplifying the T4 (CD4) receptor and the T-cell receptor mRNA sequences within the same clinical sample and quantifying the amount of those two receptors to establish the severity of T4 cell depletion in clinical samples. With respect to the beta-chain of the constant region of the T-cell receptor, the preferred target sequence is conserved in the beta 1 and beta 2 constant region sequences. This region corresponds to nucleotides 267 through 375 of the published sequence of Yoshikai, Y., et al., *Nature* 312: 521–524 (1984). For amplification of the constant region of the beta-chain of the T-cell receptor, the first primer is preferably a sense oligodeoxyribonucleotide with the sequence 5' ACTCCA- GATACTGCCTGAGC 3', the second primer if preferably an antisense oligodeoxyribonucleotide with the sequence 5' GCTATCCCTGTACGCCTCTGGC 3', and a preferred internal probe is an antisense oligodeoxyribonucleotide with the sequence 5' GGTGAGGATCTTCATGAGGTAGTC 3'.

In the following example, RNA template from the HIV 3'ORF region and the T-cell receptor beta-chain constant region were co-amplified.

EXAMPLE 6

Equal amounts of HIV 3'ORF specific primers (HTLV-A and HTLV-B) and the above-described T-cell receptor primers were mixed with 1 microgram of total RNA prepared from HIV-1 infected H9 cells. Thirty (30) amplification rounds were carried out. The first few rounds were with AMV reverse transcriptase, while the remainder of the 30 rounds were with *Taq* I DNA polymerase using the Gene-Amp Kit (Perkin-Elmer, Cetus). Electrophoresis, blotting, and hybridization were carried out as described in Example 1. The left hand panel of FIG. 9A represents four samples probed with the HIV specific probe (HTLV-C). After autoradiography, this filter was stripped of the HIV probe and reprobed with the above-described T-cell receptor internal probe (right panel).

The FIG. 9B autoradiograms were obtained by performing procedures similar to those described in Example 2 with the following exceptions. Lane a contains DNA amplified from the pGM92+21 transcript, lane b contains DNAs amplified from HIV-1 infected H9 cells, while lane c contains DNAs amplified from a diagnosed AIDS patient. In each amplification mixture, both HIV and T-cell receptor primers were present. The panel on the left represents probing with the HTLV-C probe. After stripping the probe from the filter, the filter was reprobed with the T-cell receptor probe. The residual signal in lane a in the right hand panel could not be removed by the stripping process. The black circles denote HIV sequences while the open triangle denotes the T-cell receptor sequence. In lane b of the T-cell receptor probed filter, there was a weak signal which is not visible in this reproduction.

Amplification of the T4 (CD4) receptor is carried out by using the published sequence of Maddon, P., et al., *Cell* 42: 93–104 (1985) (nucleotides 301 through 458). A preferred first amplification primer is a sense oligodeoxyribonucleotide with the sequence 5' CTGAATGATCGCGCTGACT- CAAG 3', a preferred second primer is an antisense oligodeoxyribonucleotide with the sequence 5' TTGGCAGACAATCCGAACACTAG 3'. A preferred probe is an antisense oligodeoxyribonucleotide with the sequence 5' GTATCTGAGTCTTCTATCTTAAG 3'. In the following example, T-cell receptor RNA and T4 (CD4) receptor RNA are co-amplified.

EXAMPLE 7

Figure 10A:
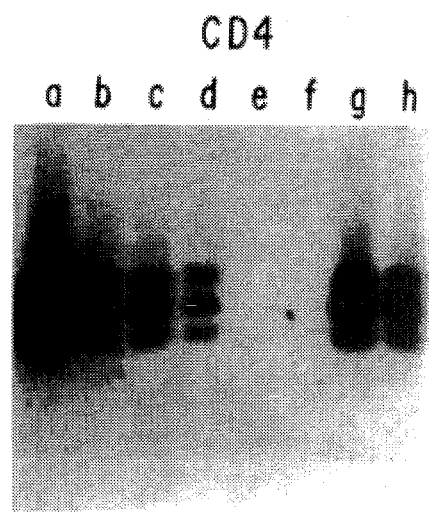
FIG. 10 shows photographs of autoradiograms of amplified T-cell receptor and T4 (CD4) receptor RNA template from various sources. The upper panel was probed with a CD4 hybridization probe while the lower panel was probed with a T-cell receptor hybridization probe.
Figure 10B:
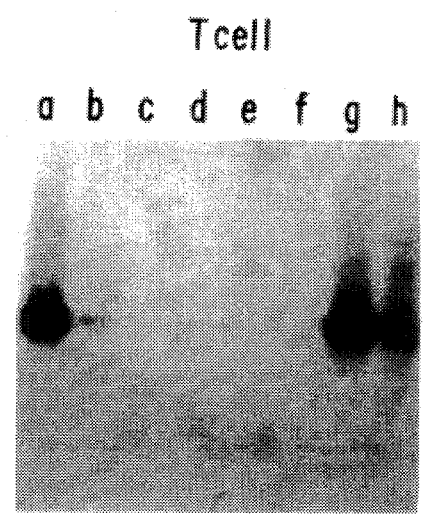

The conditions for amplification are as described in Examples 5 and 6 with the exception that the primers used are those described previously for the constant region of the beta-chain of the T-cell receptor and the T4 (CD4) receptor. The resulting autoradiograms are shown in FIG. 10. The sample sources and primers utilized for the autoradiogram lanes are as follows: (a) and (b), human peripheral lymphocyte RNAs, both T-cell receptor and CD4 receptor primers included; (c) HIV-1 infected H9 cell RNA with only CD4 primers; (d) uninfected H9 cell RNA with only CD4 primers; (e) HIV-1 infected H9 cell RNA primed only with HIV-1 5'LTR primers (hybridization to LTR probe not shown); (f) uninfected H9 cell RNA primed only with HIV-1 5'LTR primers (hybridization to LTR probe not shown); (g), HIV-1 infected H9 cell RNA primed with both T-cell receptor and CD4 receptor primers; (h) uninfected H9 cell RNA primed with both T-cell receptor and CD4 receptor primers.

The upper panel depicts hybridization of amplification product to the CD4 receptor probe. The reason for the multiple bands is not clear in this example. The lower panel represents the same filter stripped of the CD4 probe and reprobed with the T-cell receptor probe.

As seen in the FIG. 10 autoradiograms, all the expected amplification bands are present.

A further control template comprising HIV-15'LTR sequences with a small deletion or insertion can be constructed and used in a similar manner as the pGM92+21 sequence used as a control for the 3'ORF template (Example 1).

In accordance with the present invention, a recognition sequence for the T7 RNA polymerase can be appended to the 5'end of at least one of amplification primers for the 5'LTR, beta-actin, T-cell receptor, and T4 (CD4) receptor sequences to allow for transcription and amplification by T7 RNA polymerase.

Another aspect of the present invention involves non-radioactivity labeled hybridization probes with sensitivities of detection similar to that obtainable with $^{32}$P for use in detecting sequences according to the methods of the present invention. Use of non-isotopic detection methods eliminates problems attendant with the handling and disposing of radioisotopes.

For example, transcription and amplification product derived from the methods of the present invention can be detected by adding non-radioactive precursor to the transcription reaction reagents which can then be biotinylated after transcription.

Also, oligodeoxyribonucleotide probes can be synthesized with the specific required sequence, the 5' end of which sequence is attached to a reactive amino group as described by Smith, L. M., et al. *Nuc. Acids Res.* 13(7): 2399 (1985) (synthesis of oligonucleotides containing an aliphatic amino group at the 5' terminus) and Challet, A., et al., *Nuc. Acids Res.* 13(5): 1529 (1985) (labeling oligodeoxyribonucleotides with biotin via a 5' aminoalkylphosphoramide linker arm). A fluorophore, biotin, peptide or enzyme is then attached to the 5' amino group. Examples of enzyme useful as ligands for conjugation to such probes are those that take part in dye reduction such as alkaline phosphatase.

Of particular importance is the use of fluorescently tagged or biotinylated material as hybridization probes or as amplification primers for detection of HIV-1 or other amplification product as described above. Product containing the T7 promoter sequence can be transcriptionally amplified with non-radioactive nucleoside triphosphates and then hybridized with either a fluorescently tagged or biotinylated oligodeoxyribonucleotide probe which is covalently attached to an oxidizable solid support such as that available from Molecular Biosystems, Inc., San Diego, Calif. Such a support is a chemically and mechanically stable matrix which allows for synthesis of the oligonucleotide, deprotection, and subsequent modification, e.g., tagging with fluorescein.

Following hybridization of non-radioactive label to the support-bound oligonucleotide, the mixture is treated with single strand specific nucleases such as mung bean, S1, and/or ribonucleases T1 and A. The digested nucleotides are washed out, and the bound hybrids are released from the support following the manufacturer's protocol. The detection of fluorescein bound in the double stranded hybrid can be accomplished either by using DNA sequencing apparatus, HPLC with a fluorescence detector, or, under appropriate conditions, by direct visualization after spotting samples into microtiter plate wells and activating the fluorescein with the appropriate wavelength of light. Detection of biotinylated probe bound into the double stranded hybrid, can also be accomplished by dot blotting the released hybrid onto a nylon membrane and reacting the hybrid with a commercially available streptavidin-alkaline phosphatase detection system as described by Gebeyehu, G., et al., *Nucl. Acids Res.* 15: 4513–4534 (1987).

The following examples illustrate the use of biotinylated oligonucleotides and fluorescein labels.

EXAMPLE 8

Biotin-tagged synthetic oligonucleotides were used as probes for detecting amplified 3'ORF sequences. Two probes, one with two biotin molecules and one with four biotin molecules were used. Hybridization methods and washes were the same as those described above for $^{32}$P-labelled oligonucleotides. A Zeta-Probe nylon membrane was used. The DNAs for were amplified from 1 µg of RNA from HIV-1 infected H9 cells. Amplification was for 21 rounds. 50 ng of biotinylated oligonucleotide 2 were hybridized to the DNA. The biotin was detected using a commercially available biotin detection kit from Bethesda Research Laboratories.

EXAMPLE 9

FIG. 11 shows fluorescein labelled priming oligonucleotides HTLV-A and HTLV-B. As shown, the fluorescein is attached to the 5' end of the oligonucleotide. HIV-1 RNA templates were amplified as described above.

Figure 11A:
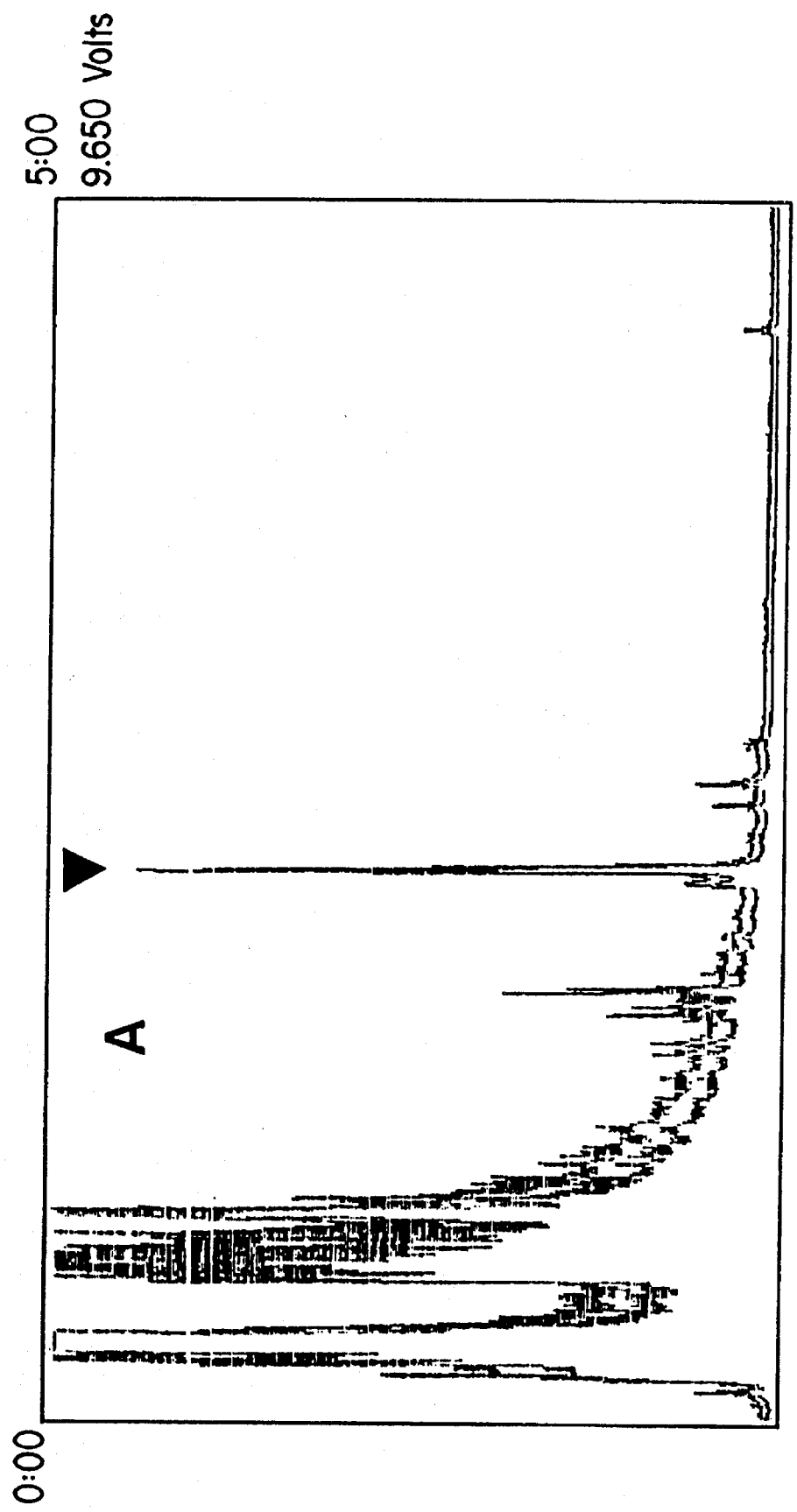
FIG. 11A shows the graphic output of a DNA sequencing apparatus showing amplified HIV-1 product.

In Panel A, the products of PCR from HIV-1 infected H9 RNAs were applied to a Dupont automated sequencing apparatus as described above. This particular sample was not visible to the naked eye via its flouresence. An aliquot (approximately 1/10th of the amplification mixture) was analyzed and the graphic output is shown in FIG. 11A. The position of the peak corresponding to the expected 151 base pair amplified product is denoted by the arrowhead.

Figure 11B:
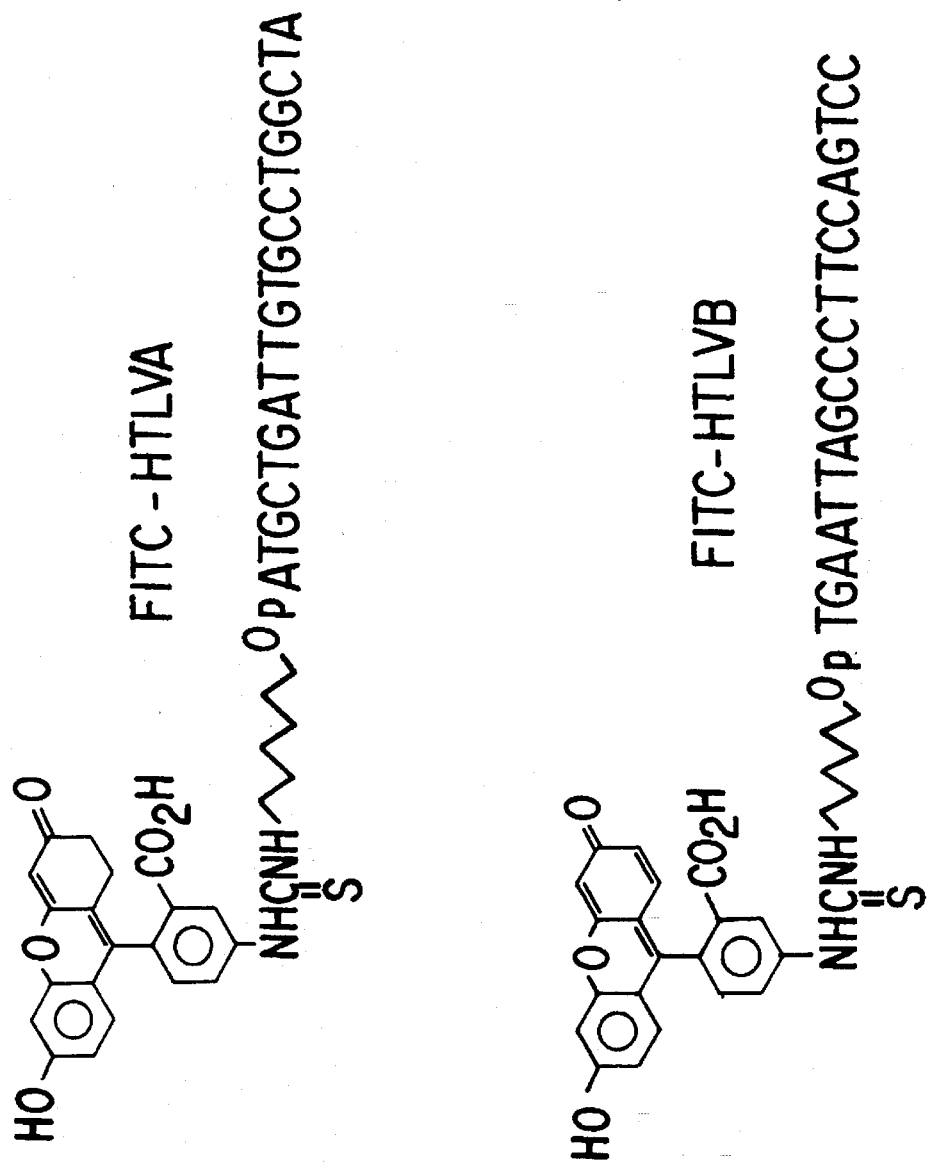
FIGS. 11B and 11C show photographs of, respectively, an ethidium bromide stained agarose gel containing HpaII digested pBR322 co-electrophoresed as a molecular weight standard, and a UV visualized agarose gel containing amplified product from pGM92+21 RNA template.
Figure 11C:
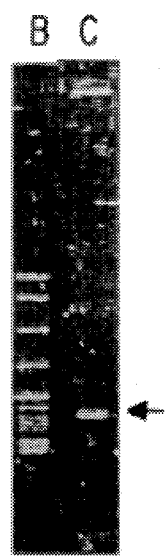

FIG. 11C shows amplified product which was visualized directly via its green fluorescence in an agarose gel on a UV transilluminating apparatus (390 nm wavelength). FIG. 11B is an ethidium bromide stained marker of HpaII digested pBR322 co-electrophoresed as a molecular weight standard. The expected size of the amplified product in this case is 172 nucleotides since the starting material was approximately 50 nanograms of RNA produced from pGM92+21. Using the DuPont sequencer with its laser beam flourescent detector, the sensitivity is approximately equivalent to that obtained with $^{32}$P.

I claim:

1. A method which comprises:

(i) providing a sequence of an HIV-1 RNA present in a human blood sample;

(ii) providing a cellular marker sequence which is a beta actin sequence or a T-cell receptor constant region beta chain sequence or a T4 receptor sequence;

(iii) simultaneously subjecting said sequence of said HIV-1 RNA and said cellular marker nucleic acid sequence to amplification by the polymerase chain reaction to produce a polymerase chain reaction amplification product;

(iv) determining whether said polymerase chain reaction amplification product contains an amplification product of said sequence of said HIV-1 RNA; and (v) determining whether said polymerase chain reaction amplification product contains an amplification product of said cellular marker nucleic acid sequence;

wherein the absence in said polymerase chain reaction amplification product of an amplification product of said sequence of an HIV-1 RNA and also of an amplification product of said cellular marker nucleic acid sequence indicates that said absence of said amplification product of said sequence of an HIV-1 RNA is a false negative reading.

2. A method which comprises:

(i) providing a sequence of an HIV-1 RNA extracted from lymphocytes isolated from peripheral blood;

(ii) providing a cellular marker sequence which is a beta actin sequence or a T-cell receptor constant region beta chain sequence or a T4 receptor sequence;

(iii) simultaneously subjecting said sequence of said HIV-1 RNA and said cellular marker nucleic acid sequence to amplification by the polymerase chain reaction to produce a polymerase chain reaction amplification product;

(iv) determining whether said polymerase chain reaction amplification product contains an amplification product of said sequence of said HIV-1 RNA; and (v) determining whether said polymerase chain reaction amplification product contains an amplification product of said cellular marker nucleic acid sequence;

wherein the absence in said polymerase chain reaction amplification product not only of an amplification product of said sequence of an HIV-1 RNA and also of an amplification product of said cellular marker nucleic acid sequence indicates that said absence of said amplification product of said sequence of an HIV-1 RNA in said polymerase chain reaction amplification product is a false negative reading.

3. A method which comprises:

(i) providing a sequence of an HIV-1 RNA present in a human blood sample;

(ii) providing a cellular marker nucleic acid sequence which is a beta actin sequence or a T-cell receptor constant region beta chain sequence or a T4 receptor sequence;

(iii) simultaneously subjecting said sequence of said HIV-1 RNA and said cellular marker nucleic acid sequence to amplification by the polymerase chain reaction to produce a polymerase chain reaction amplification product;

(iv) providing a probe complementary to said polymerase chain reaction amplification product of said HIV-1 sequence and a probe complementary to said polymerase chain reaction amplification product of said cellular marker nucleic acid sequence;

(v) subjecting said amplification products to hybridization with said probes;

(vi) determining whether the hybridization products contain said amplification products of said sequence of HIV-1 and said cellular marker sequence;

wherein the absence in said hybridization products of an amplification product of said sequence of HIV-1 RNA and also of said amplification product of said cellular marker sequence indicates that said absence of an HIV-1 RNA in said polymerase chain reaction amplification products is a false negative result.

4. A method which comprises:

(i) providing a human blood or tissue sample;

(ii) providing at least one portion of an HIV-1 RNA sequence present in said human blood or tissue sample;

(iii) providing a cellular marker nucleic acid sequence which is a beta actin sequence or a T-cell receptor constant region beta chain sequence or a T4 receptor sequence;

(iv) simultaneously subjecting said at least one portion of an HIV-1 RNA sequence present in said human blood or tissue sample and said cellular marker nucleic acid sequence to amplification by the polymerase chain reaction to produce a polymerase chain reaction amplification product;

(v) determining whether said polymerase chain reaction amplification product contains an amplification product of said at least one portion of said HIV-1 RNA sequence; and (vi) determining whether said polymerase chain reaction amplification product contains an amplification product of said cellular marker nucleic acid sequence;

wherein the absence in said polymerase chain reaction amplification product of an amplification product of said single portion of an HIV-1 RNA sequence and also of an amplification product of said cellular marker nucleic acid sequence indicates that said absence of said amplification product of said single portion of an HIV-1 RNA sequence is a false negative result.

5. The method of claim 1 or claim 3 in which at least one of the primers utilized in said polymerase chain reaction amplification of step (iii) includes a 5' recognition site for an RNA polymerase.

6. A method for detecting a false positive result in a PCR amplification and detection assay comprising:

(a) providing a first nucleic acid sequence which may contain a target sequence;

(b) providing a second nucleic acid sequence, wherein the second nucleic acid sequence is the same as the first nucleic acid sequence except that the number of nucleotides in the second nucleic acid sequence is different from the number of nucleotides in the first nucleic acid sequence;

(c) simultaneously amplifying said first and second nucleic acid sequences by PCR with the same primers to provide amplification products that differ in their numbers of nucleotides;

(d) determining whether each of said first and second nucleic acid sequences is present in said amplification product, wherein the presence of said first nucleic acid sequence and the absence of said second nucleic acid sequence indicates a false positive result.

7. The claim 6 method in which at least one primer of said pair of primers has a 5' terminal label which is a fluorophore or a radioisotope and in which step (d) is performed by determining whether said 5' terminal label is present in said amplification product.

8. A method for detecting a false positive result in a PCR amplification and detection assay comprising:

(a) obtaining HIV-1 RNA from human blood or tissue;

(b) providing a first RNA sequence which may contain a target sequence from said HIV-1 RNA obtained in step (a);

(c) providing a second RNA sequence, wherein the second RNA sequence is the same as the first RNA sequence except that the number of nucleotides in the second RNA sequence is different from the number of nucleotides in the first RNA sequence;

(d) simultaneously amplifying said first and second RNA sequences by PCR with the same primers to provide amplification products that differ in their numbers of nucleotides; and (e) determining whether each of said first and second RNA sequences is present in said amplification product, wherein the presence of said first RNA sequence and the absence of said second RNA sequence indicate a false positive result.

9. A method for determining a false positive result in a PCR amplification and detection assay comprising:

(a) simultaneously amplifying by PCR a first HIV-1 RNA sequence and a second HIV-1 RNA sequence wherein (i) said second HIV-1 RNA sequence contains more or fewer nucleotides than said first HIV-1 RNA sequence; and (ii) said first and second HIV-1 RNA sequences are amplified by PCR to provide amplification products that differ in their number of nucleotides; and (b) determining whether each of said first and second HIV-1 RNA sequence is present in said amplification product, wherein the presence of said first HIV-1 RNA sequence and the absence of said second HIV-1 RNA sequence indicates a false positive result.

10. The claim 9 method in which said first sequence of HIV-1 RNA is from the 3' ORF or 5' LTR portion of HIV-1 RNA.

11. The method of claim 6, in which said second nucleic acid sequence has more nucleotides than said first nucleic acid sequence.

12. The method of claim 6, in which said second nucleic acid sequence has 21 more nucleotides than said first nucleic acid sequence.

13. The method of claim 6, in which said first nucleic acid sequence is a 3 ORF HIV-1 sequence and said second nucleotide is a 5' LTR HIV-1 sequence which has more or less nucleotides than said first nucleic acid sequence.

14. The method of claim 8, in which said second RNA sequence has more nucleotides that said first RNA sequence.

15. The method of claim 8, wherein said second RNA sequence has 21 or more nucleotides than said first RNA sequence.

16. The method of claim 8, wherein said first RNA sequence is a 3' ORF HIV-1 sequence and said second RNA sequence is a 5' LTR HIV-1 sequence which has more or fewer nucleotides than said first RNA sequence.

* * * * *